(12) United States Patent (10) Patent No.: US 9,957,476 B2
Gunn-Moore et al. (45) Date of Patent: May 1, 2018

(54) CELL PORATION

(75) Inventors: Frank Gunn-Moore, Fife (GB);
Kishan Dholakia, Fife (GB);
Yoshihiko Arita, Fife (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 876 days.

(21) Appl. No.: 13/639,296

(22) PCT Filed: Apr. 11, 2011

(86) PCT No.: PCT/GB2011/000553
§ 371 (c)(1),
(2), (4) Date: Jan. 4, 2013

(87) PCT Pub. No.: WO2011/124899
PCT Pub. Date: Oct. 13, 2011

(65) Prior Publication Data
US 2013/0113140 A1 May 9, 2013

(30) Foreign Application Priority Data
Apr. 9, 2010 (GB) .................................. 1005926.9

(51) Int. Cl.
*C12N 5/00* (2006.01)
*C12M 1/42* (2006.01)
*C12N 15/87* (2006.01)
(52) U.S. Cl.
CPC ........... *C12N 5/0006* (2013.01); *C12M 35/02* (2013.01); *C12N 15/87* (2013.01)
(58) Field of Classification Search
None
See application file for complete search history.

(56) References Cited

U.S. PATENT DOCUMENTS 8,338,776 B2 * 12/2012 Walt ................... G02B 17/0615
250/201.3
2013/0113140 A1 5/2013 Gunn-Moore et al.

FOREIGN PATENT DOCUMENTS

EP 2556149 B1 11/2016

OTHER PUBLICATIONS

McDougall, et al. (Apr. 1, 2009 online) "Targeted optical injection of gold nanoparticles into single mammalian cells", Journal of Biophotonics, 2(12): 736-43.*
Arita, et al. (Mar. 2, 2011 online) "Spatially optimized gene transfection by laser-induced breakdown of optically trapped nanoparticles", Applied Physics Letters, 98, article 093702, pp. 1-3.*

Barnes, Peter A., et al., "Laser Induced Underwaters Sparks", Applied Physics Letters, 1968, vol. 13, No. 8, pp. 282-284.
Benjamin, T. B., et al., "The Collapse of Cavitation Bubbles and the Pressures thereby Produced against Solid Boundaries", Phil. Trans. R. Soc. Lond. A, 1966, vol. 260, pp. 221-240.
Feril, Loreto B., et al., "Enhancement of Ultrasound-Induced Apoptosis and Cell Lysis by Echo-Contrast Agents", Ultrasound in Med. & Biol., 2003, vol. 29, No. 2, pp. 331-337.
Hellman, Amy N., et al., "Biophysical response to pulsed laser microbeam-induced cell lysis and molecular delivery", J. Biophoton, 2008, No. 1, pp. 24-35.
Hentschel, W., et al., "Acoustic emission of single laser-produced cavitation bubbles and their dynamics", Applied Scientific Research, 1982, vol. 38, pp. 225-230.
Honda, Hidemi et al., "Role of Intracellular Calcium Ions and Reactive Oxygen Species in Apoptosis Induced by Ultrasound", Utrasound in Med. & Biol., 2004, vol. 30, No. 5, pp. 683-692.
Hougen, J. T., et al., "Laser-Induced High-Pressure Shock Waves in Water", 1967, vol. 10, No. 2, pp. 46-48.
Miller, Douglas L., et al., "Tumor Growth Reduction and DNA Transfer by Cavitation-Enhanced High-Intensity Focused Ultrasound In Vivo", Ultrasound in Med. & Biol., 2003, vol. 29, No. 6, pp. 887-893.
Pitsillides, Costas M., et al., "Selective Cell Targeting with Light-Absorbing Microparticles and Nanoparticles", Biophysical Journal, 2003, vol. 84, pp. 4023-4032.
Prentice, Paul et al., "Membrane disruption by optically controlled microbuble cavitation", Nature Physics, 2005, vol. 1, pp. 107-110.
Rau, Kaustubh R., et al., "Pulsed Laser Microbeam-Induced Cell Lysis: Time-Resolved Imaging and Analysis of Hydrodynamic Effects", Biophysical Journal, 2006, vol. 91, pp. 317-329.
Soughayer, Joseph S., et al., "Characterization of Cellular Optoporation with Distance", Anal. Chem., 2000, vol. 72, pp. 1342-1347.
Tirlapur, Uday K., et al., "Targeted transfection by femtosecond laser", Nature, 2002, vol. 418, pp. 290-291.
Tsampoula, X., et al., "Femtosecond cellular transfection using a nondiffracting light beam", Applied Physics Letters, 2007, Letter 91.
Umebayashi, Yukihiro et al., "Elevation of Plasma Membrane Permeability on Laser Irradiation of Extracellular Latex Particles", J. Biochem, 2003, vol. 134, pp. 219-224.
Vogel, Alfred et al., "Femtosecond-Laser Induced Nanocavitation in Water: Implications for Optical Breakdown Threshold and Cell Surgery", Physical Review Letters, 2008, PRL 100.
Yao, Cuiping et al., "Elevation of plasma membrane permeability by laser irradiation of selectively bound nanoparticles", Journal of Biomedical Optics, 2005, vol. 10, No. 6.
Yao, Cuiping et al., "Influence of laser parameters on nanoparticle-induced membrane permeabilization", Journal of Biomedical Optics, 2009, vol. 14, No. 5.
Yao, Cui-Ping et al., "Laser-Based Transfection and Gene Therapy", IEEE Transactions on Nanobioscience, 2008, vol. 7, No. 2, pp. 111-119.

(Continued)

*Primary Examiner* — Robert M Kelly
(74) *Attorney, Agent, or Firm* — Moore & Van Allen PLLC; W. Kevin Ransom

(57) ABSTRACT

A method for porating one or more cells comprising positioning a particle near each cell; and causing laser-induced breakdown of the particle to create one or more cavitations, wherein the cavitation(s) causes poration of the cell.

27 Claims, 10 Drawing Sheets
(8 of 10 Drawing Sheet(s) Filed in Color)

(56) References Cited

OTHER PUBLICATIONS

International Search Report for International Application No. PCT/GB2011/000553 dated Aug. 23, 2011.
Canadian Office Action for Application No. 2,795,498 dated Aug. 16, 2017.

* cited by examiner

CELL PORATION

FIELD OF THE INVENTION

The present invention relates to a system and method for targeted membrane poration of biological cells and tissues in a specific area, and large scale poration of those in a wide area with microbubbles excited by the laser-induced breakdown of optically trapped single nanoparticles.

BACKGROUND OF THE INVENTION

A number of mechanisms are known for allowing transient poration of cells for the introduction of therapeutic agents. Recently, this has included a suite of optical methods, which add the potential of sterility, reconfigurability and single cell selectivity. For example, high repetition rate (~80 MHz) femtosecond laser pulses of low average power (<100 mW) can be used to create low density plasmas at a focus that react with the cell's lipid bilayer causing transient pores to be generated, see Vogel, A., Linz, N., Freidank, S. and Paltauf, G., Phys Rev Lett 100 (3), 0381021-0381024 (2008). They are suitable for membrane poration of cells achieving high transfection efficiency of up to 80% with an acceptable cell viability of ~80%, as described by Tirlapur, U. K. and Konig, K., Nature 418 (6895), 290-291 (2002) and Tsampoula, X. et al., Appl Phys Lett 91 (5), 053902 (2007). However, this approach requires the precise positioning of the laser focus on the cell membrane and is unsuitable for a high-throughput transfection system.

Cavitation bubbles can also play an important role in plasma membrane poration. It is known that acoustic bubbles oscillated by ultrasonic irradiation (insonation) can lead to enhanced membrane permeabilization (sonoporation) of cells. This is described in the art, see for example: Feril, L. B. et al., Ultrasound Med Biol 29 (2), 331-337 (2003); Miller, D. L. and Song, J. M., Ultrasound Med Biol 29 (6), 887-893 (2003); Honda, H., Kondo, T., Zhao, Q. L., Feril, L. B. and Kitagawa, H., Ultrasound Med Biol 30 (5), 683-692 (2004), and Prentice, P., Cuschierp, A., Dholakia, K., Prausnitz, M. and Campbell, P., Nat Phys 1 (2), 107-110 (2005). When cavitation occurs near a rigid boundary such as a cell membrane, the bubbles tend to collapse asymmetrically, often forming high speed liquid jets directed toward the wall that can cause localized membrane poration, thus allowing the uptake of molecules by these cells (Benjamin, T. B. and Ellis, A. T., Philos Tr R Soc S-A 260 (1110), 221-245 (1966)). However, this approach often activates multiple cavitation bubbles, which lead to non-uniform and sporadic molecular uptake that lacks refined spatial control.

Cavitation bubbles can be produced by the optical breakdown or ablation of an absorptive medium (see Barnes, P. A. and Rieckhof, K. E., Appl Phys Lett 13 (8), 282-284 (1968) and Bell, C. E. and Landt, J. A., Appl Phys Lett 10 (2), 46-48 (1967)). Of the approaches devised to date, membrane permeabilization of cells has been achieved at the expense of a significant amount of cell lysis owing to the relatively high breakdown threshold of the absorptive substances used in this procedure, e.g. water (present in the medium) or silica (glass coverslips) resulting in a much larger cavitation bubble (millimeters in diameter) compared to cell size (tens of micrometers) See Hellman, A. N., Rau, K. R., Yoon, H. H. and Venugopalan, V., J Biophotonics 1 (1), 24-35 (2008); Rau, K. R., Quinto-Su, P. A., Hellman, A. N. and Venugopalan, V., Biophys J 91 (1), 317-329 (2006), and Soughayer, J. S. et al., Anal Chem 72 (6), 1342-1347 (2000).

SUMMARY OF THE INVENTION

The present invention relates to targeted membrane poration of cells in a specific area and large scale poration of those in a wide area with microbubbles excited by the laser-induced breakdown of optically trapped single nanoparticles. Poration of the cell membrane ideally creates an opening through the cell (typically the opening is temporary, and with time it closes over).

When light, for example from a Q-switched laser operating with nanosecond laser pulses, is focused onto an optically trapped single nanoparticle, laser-induced breakdown can take place, leading to the formation of plasma and emission of shockwaves by its expansion followed by the vaporization of the nanoparticle or liquid (surrounding aqueous medium). This vapor volume effectively constitutes a cavitation bubble, which expands as the volume of the ablated nanoparticle or vaporized liquid increases. Bubble expansion and its subsequent collapse can be accompanied by the emission of acoustic transients and microjetting depending on the position of the cavitation bubble relative to the substrate. These photomechanical properties can lead to the permeabilization of plasma membrane of cells.

The jet formation and emission of the acoustic transients upon collapse depend on the dimensionless stand-off parameter, $\gamma$ between the bubble and wall, $\gamma = Z_0/R_{max}$, where $Z_0$ is the distance between the bubble/nanoparticle centre and the wall, and $R_{max}$ is the maximum bubble radius (Hentschel, W. and Lauterborn, W., Appl Sci Res 38, 225-230 (1982)). When $\gamma \leq 1$ (i.e. the bubble wall is in contact with the boundary.), the jet formation is predominant compared to the acoustic emission. On the other hand, when $\gamma \gg 1$, (i.e. the bubble is free from distortion.), the bubble energy is more efficiently transformed into acoustic energy. Thus, the jet can cause localized membrane poration of multiple cells in a targeted zone, while the acoustic transients can yield large scale poration of cells in a wide area (hundreds of micrometers) as the acoustic waves can propagate a long distance (typically hundreds of micrometers) in the sample medium.

It is important to control the volume/size of cavitation (determines the total bubble energy available for the jet and acoustic energies) as well as its axial position from the boundary (determines the relative intensity between the jet and acoustic emissions). Optical tweezers allow the confinement and positioning of micro- and nano-particles at a desired location within the sample. With this approach, the threshold energy required for LIB is dependent on the nanoparticle material and its size and is free from the surrounding medium. Thus, the technique can optimize the bubble energy and stand-off parameter $\gamma$, which lead to membrane permeabilization of mammalian cells with retention of cell viability.

In summary, the method of the invention has the potential to increase the applicability of optically controlled cell transfection. The technique only requires a modest nanosecond laser pulse energy, reduces cell lysis, and operates in a spatially selective manner. It offers major advantages due to its simplicity, lower cost, and higher reliability when compared to existing methods.

The method of the invention may further involve introducing, or allowing to be introduced, a material into the porated cell. The material that is to be introduced may be a fluid.

Multiple nanoparticles may be provided and the method involves simultaneously causing laser-induced breakdown of the multiple particles.

An optical element may be used to generate multiple beams from a single laser source for trapping the multiple particles.

An optical element may be used to generate multiple beams from a single laser source for causing laser induced breakdown of the multiple particles.

An optical element may be used to generate multiple beams from a single laser source for causing laser induced breakdown of the multiple particles. The same optical element may be used to generate multiple beams from another laser source for causing laser induced breakdown of the multiple particles.

The optical element may a diffractive optical element, for example a spatial light modulator, or an acousto optic deflector.

The method may involve positioning the particle close to a hard surface before causing laser induced breakdown.

The particle may have a dimension of 1 micrometer; preferably less than or equal to 500 nm. The particle may have a sized to match the diffraction limited focal spot size of the breakdown laser.

The particle may be made of any suitable material, for example a material selected from: silica; polystyrene; latex; gold; silver; carbon. The particle may be shaped as a sphere or shell or rod.

According to another aspect of the invention, there is provided a system for porating one or more cells comprising means for positioning a particle near the or each cell; and means for causing laser-induced breakdown of the particle to create one or more cavitations, wherein the cavitation(s) causes poration of the cell.

The patent or application file contains at least one drawing executed in color. Copies of this patent or patent application publication with color drawings will be provided by the Office upon request and payment of the necessary fee.

BRIEF DESCRIPTION OF THE DRAWINGS

Various aspects of the invention will now be described by way of example only and with reference to the accompanying drawings, of which.

DESCRIPTION OF THE DRAWINGS

The present invention involves optical trapping of single nanoparticles using lasers. For example, optical tweezers can be used to confine and position micro- and nanoparticles at a desired location within a sample. This is done in the vicinity of a cell that has to be porated. Once located and trapped in the appropriate position, the particle is exposed to laser radiation of a nanosecond pulse to cause laser-induced breakdown. This optical breakdown causes, in turn, the formation of a cavitation bubble that can produce a jet flow and/or acoustic transients for porating the cell of interest. With this approach, the threshold energy required for laser-induced breakdown is dependent on the nanoparticle material and its size and is free from the surrounding medium (typically water or a water based fluid). Thus, this technique can optimize cavitation and can be used for many applications, for example plasmid-DNA transfection of mammalian cells, with good retention of cell viability.

In general, the optical breakdown of a nanoparticle causes the formation of a cavitation bubble, which results in both a fluid jet and/or acoustic transients upon collapse. However, by varying one or more parameters, one of these can be encouraged to dominate. This allows a degree of control over the poration process.

The jet formation and emission of the acoustic transients depend on the dimensionless stand-off parameter, γ between the bubble and wall, $$\gamma = Z_0/R_{max},$$

where $Z_0$ is the distance between the bubble/nanoparticle centre and the wall and $R_{max}$ is the maximum bubble radius (Hentschel, W. and Lauterborn, W., *Appl Sci Res* 38, 225-230 (1982)). When $\gamma \leq 1$ (i.e. the bubble wall is in contact with the boundary.), the jet formation is predominant compared to the acoustic emission. On the other hand, when $\gamma \gg 1$, (i.e. the bubble is free from distortion.), the bubble energy is more efficiently transformed into acoustic energy.

Figure 1:
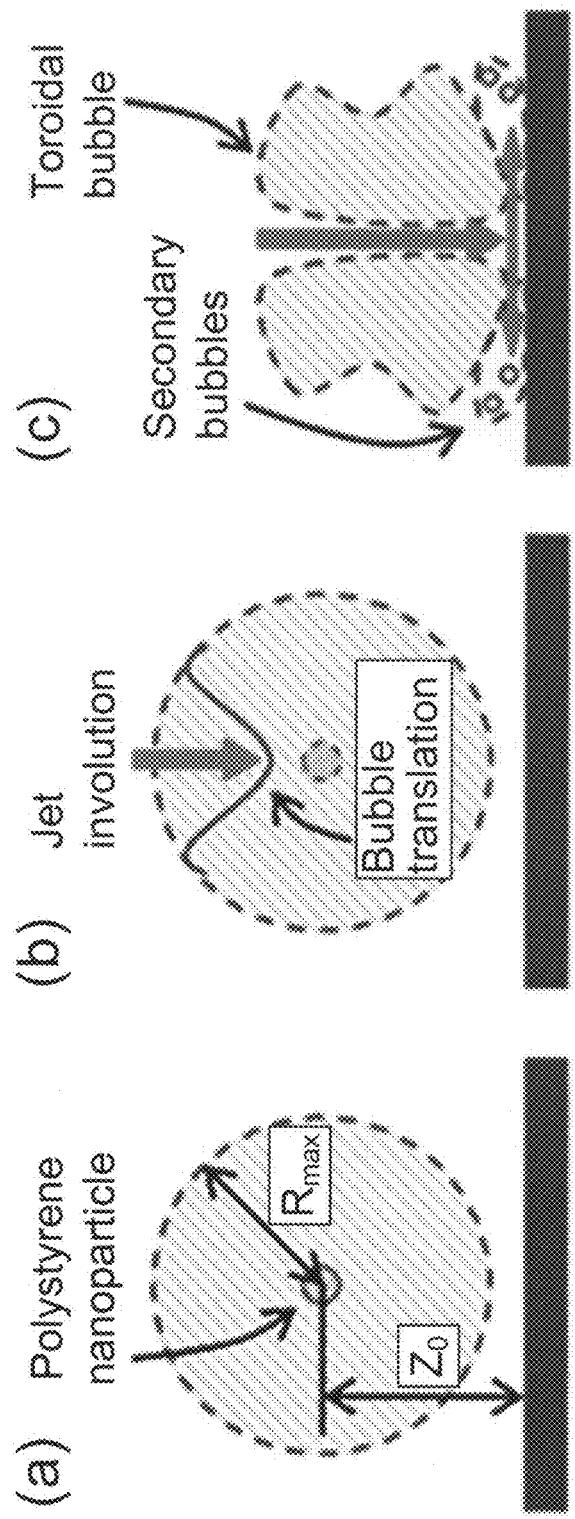
FIG. 1 shows various stages in the formation of a bubble using laser-induced breakdown of a nanoparticle, and the collapse of the bubble to form a jet.

FIG. 1 shows three stages in the formation of a bubble using laser-induced breakdown of a nanoparticle. In this case, the nanoparticle is in a fluid, e.g. water, and is positioned relatively close to a hard substrate ($\gamma \sim 1$). This arrangement is designed to encourage the formation of a jet of fluid. FIG. 1(a) shows the start of the process. Here, the nanoparticle has been trapped relatively close to the substrate and exposed to laser light to cause optical breakdown. This causes plasma to form, which vaporizes the nanoparticle as well as its surrounding water and creates a vapour bubble which expands rapidly. After an initial period of expansion, the bubble starts to collapse. Because the bubble is relatively close to the substrate, its collapse is asymmetric, as shown in FIG. 1(b). This causes the bubble to move down towards the substrate. Further collapse results in the formation of a jet flow, which traverses the bubble volume, which leads to a donut or toroidal shaped bubble, as shown in FIG. 1(c).

Figure 2:
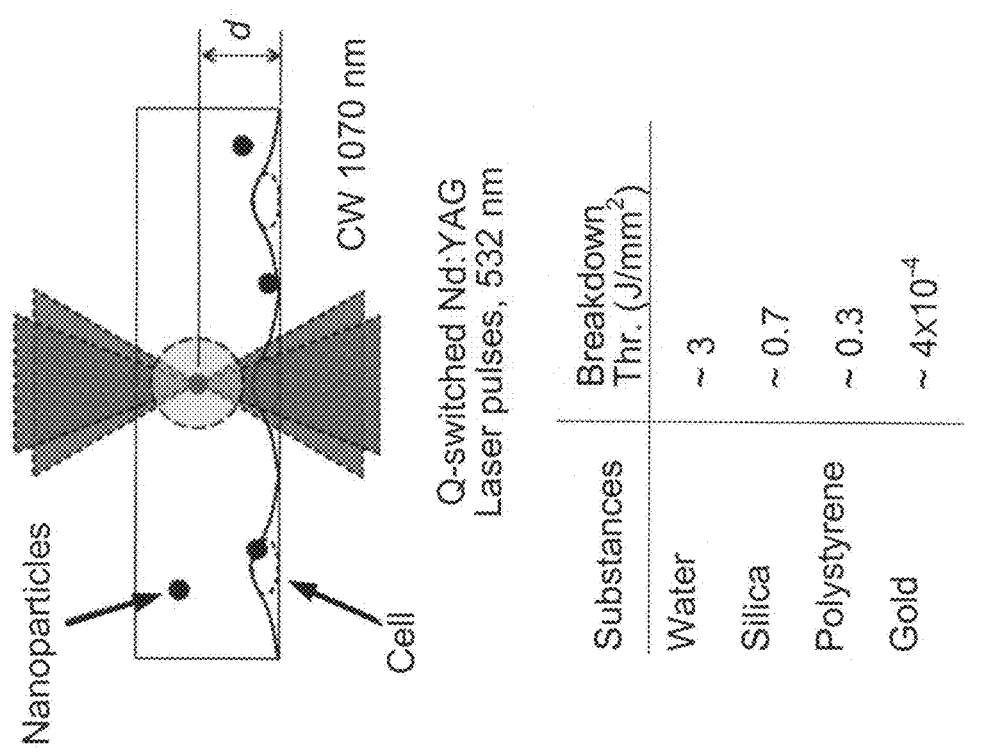
FIG. 2 is an illustration of a nanoparticle trapped in the vicinity of a cell that is to be porated using laser-induced breakdown of the nanoparticle.

FIG. 2 shows a schematic of the laser-induced breakdown of an optically trapped single nanoparticle in proximity to a plurality of cells. In this case, a single nanoparticle is trapped in an optical trap in the vicinity of a cell that has to be porated. By varying the axial position of the trapped particle, the stand-off parameter, γ can be adjusted, and so the effect of the collapse of the cavitation can be controlled. As noted above, if the nanoparticle is trapped close to the cell (γ≤1), then on laser-induced breakdown, a jet dominates allowing the poration of cells in a localized area. If nanoparticle is trapped relatively further away from the cells (γ>>1), then on laser-induced breakdown, acoustic transients dominate allowing the poration of multiple cells in a wide area.

The required energy (i.e. the threshold energy) for laser-induced breakdown or cavitation is dependent on the absorption cross-section of the material of the nanoparticle. By introducing nanoparticles, the energy required for laser-induced breakdown can be reduced compared with prior art arrangements that rely on the breakdown the medium in which the cells are present, typically water. The breakdown thresholds for various materials are shown in FIG. 2. By using nanoparticles with relatively low breakdown thresholds (for example less than 1 $J/mm^2$), the transfer of photon energy required to cause breakdown is reduced and consequently the cavitation volume/size is reduced. The nanoparticle size can also affect the cavitation volume/size, as the volume of the vaporised nanoparticle effectively constitutes a cavitation bubble. Hence, the size of the cavitation or bubble can be controlled by selection of the material and/or size of the nanoparticle.

Figure 3:
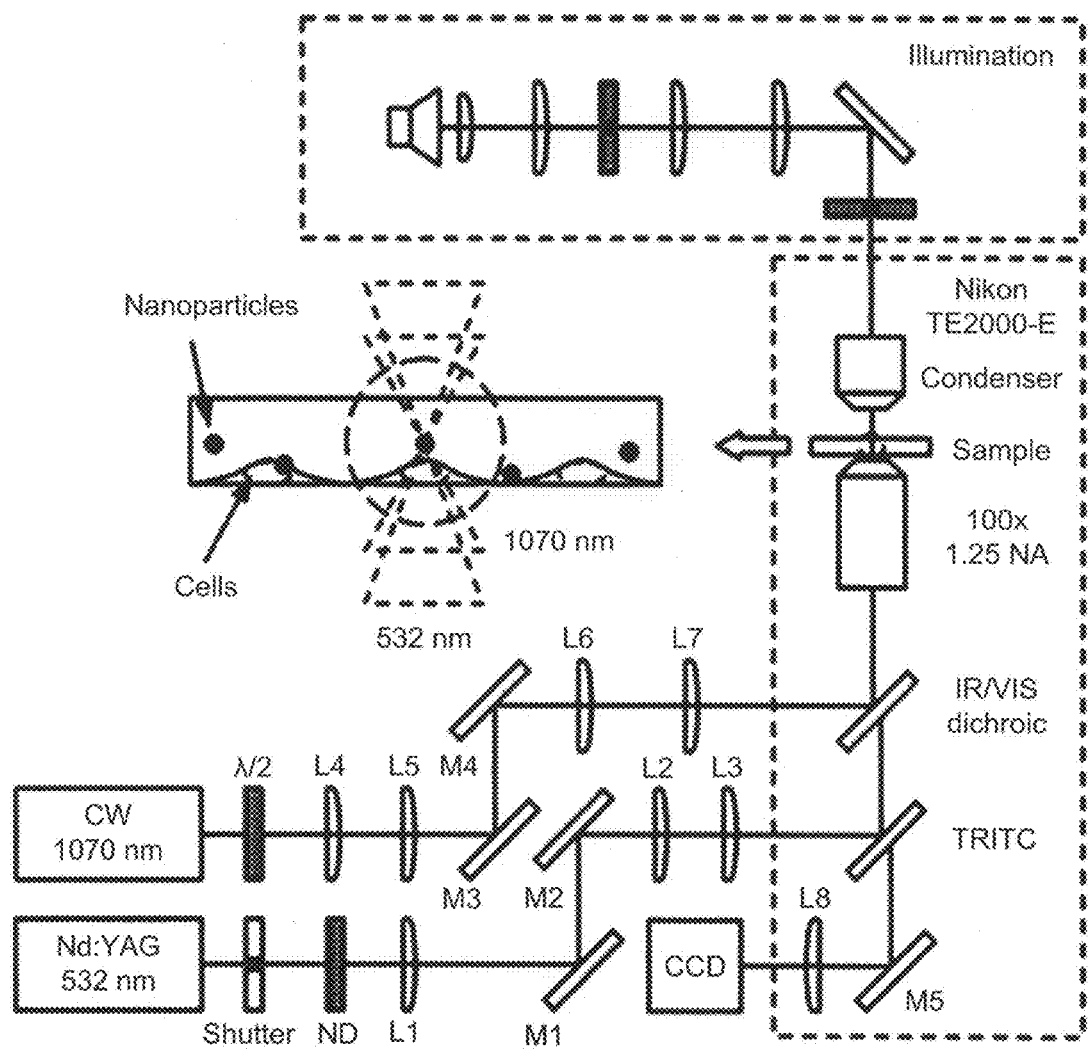
FIG. 3 is a schematic diagram of an optical arrangement for trapping and causing laser-induced breakdown of a nanoparticle.

Various experiments have been done to test the effectiveness of cell poration. FIG. 3 shows an experimental set-up having a laser for causing laser-induced breakdown of a nanoparticle and a laser for forming an optical trap for positioning the nanoparticle. In particular, the system of FIG. 3 has a 1070 nm CW fiber laser (IPG Laser GmbH, YLM-5-1070-LP: power of ~100 mW) was focused by a microscope objective (Nikon Ltd., E plan 100×1.25 numerical aperture (NA)/oil) to optically trap a polystyrene nanoparticle (from 400 nm to 2 μm in diameter) within the buffer medium. The nanoparticle was manipulated to a predefined location between 0 and 25 μM above the plane of the cell monolayer. Techniques for optically trapping and manipulating particles are well known and so will not be described herein in detail. Once in position, a 532 nm frequency doubled Q-switched Nd:YAG laser (Elforlight Ltd., SPOT: pulse width of ~1 ns, energy of ~1 μJ, and repetition rate of 1 kHz) was coaligned with the trapping beam and focused through the same objective onto the trapped nanoparticle for 40 ms to effect laser-induced breakdown.

Figure 4:
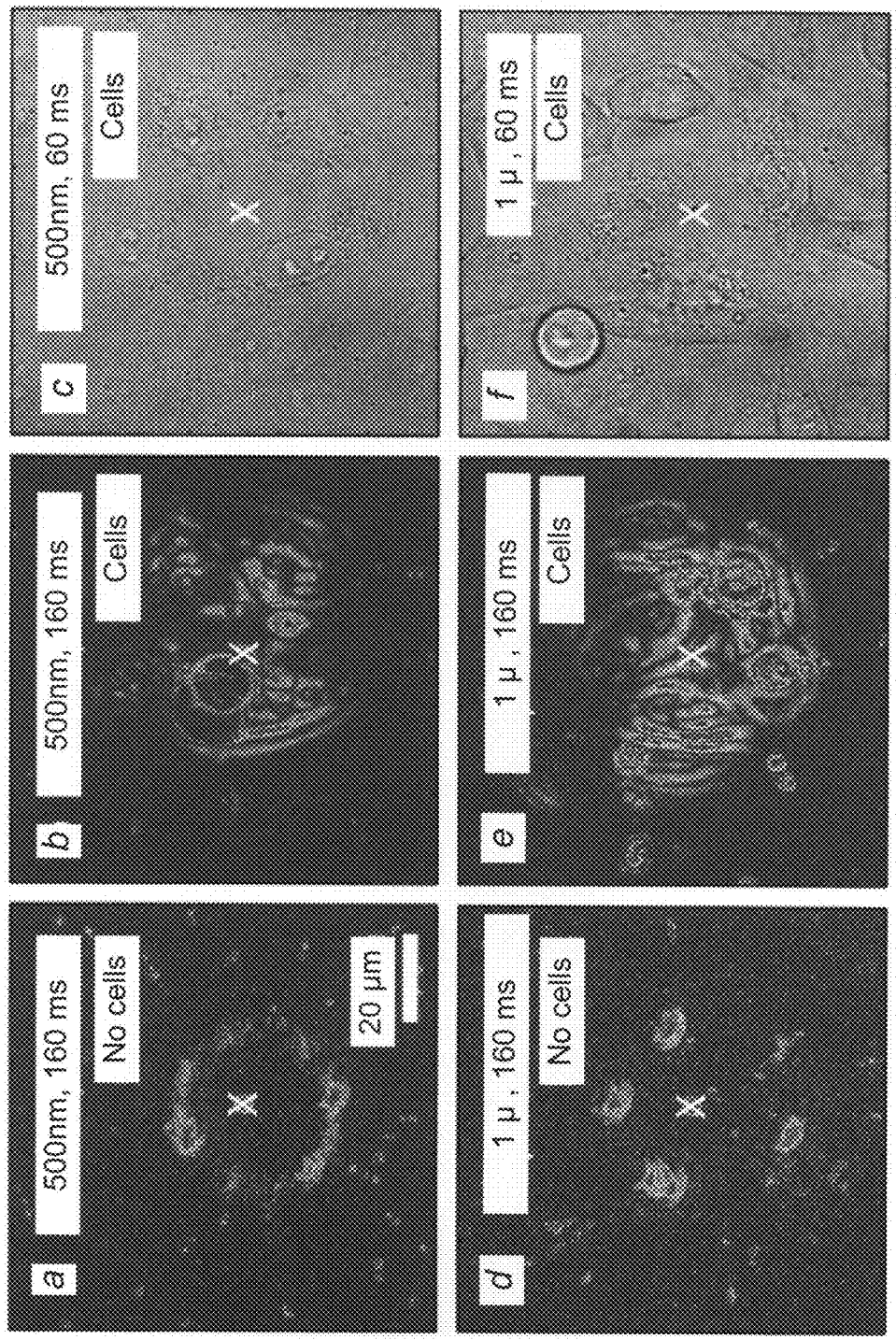
FIG. 4 shows residual gas bubbles by the laser-induced breakdown of 500 nm and 1 μm nanoparticles and the subsequent cellular response.

FIG. 4 shows the formation of residual gas bubbles by the laser-induced breakdown of 500 nm and 1 μm nanoparticles and the subsequent cellular response. FIGS. 4 (a) and (d) show residual gas bubbles formed in the deionized water over 160 ms after laser-induced breakdown. FIGS. 4 (b) and (e) show the displacements of cells by the laser-induced breakdown in the presence of a CHO-K1 cell monolayer. FIGS. 4 (c) and (f) show changes in cell morphology, 60 s after laser-induced breakdown. In the Figures, 'x' denotes the location of laser-induced breakdown.

In the presence of a CHO-K1 cell monolayer, the cellular area affected by the laser-induced breakdown of a 500 nm nanoparticle was smaller ~40 μm (FIG. 4(b)) than that of a 1 μm nanoparticle, ~60 μM (FIG. 4(e)) in diameter. A large displacement of cells from the laser-induced breakdown of a 1 μm nanoparticle, was indicated by an intense signal (FIG. 4(e)) resulting in three or more cells undergoing lysis (FIG. 4(f)) while changes in cell morphology with the laser-induced breakdown of a 500 nm nanoparticle were characterized by granulation and nucleus condensation (FIG. 4(c)).

From these experiments, it can be seen that the kinetic jets have the potential to damage the surface, which leads to the appearance of circular clearance zones in the cell covered substrates (FIG. 4 (c),(f)). The physical perturbations to these cells can be optimized by the nanoparticle material, its size, and its axial location from the cell monolayer.

Figure 5:
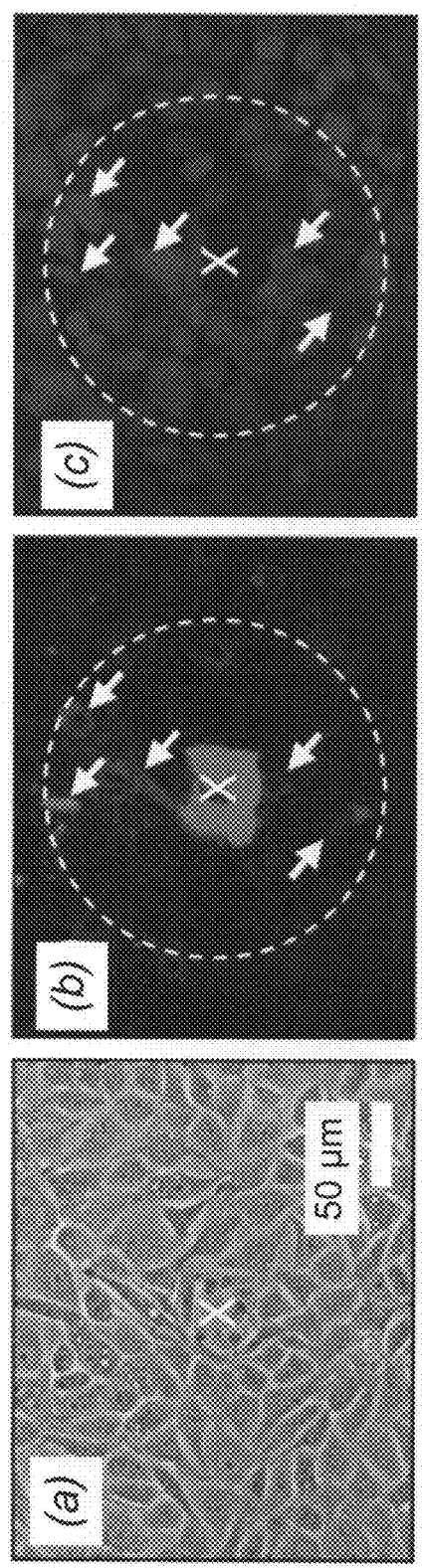
FIG. 5 shows molecular injection of Propidium iodide (PI) into CHO-K1 cells by the laser-induced breakdown of a 500 nm nanoparticle, and cell viability assay using Calcein-AM (CAM)

FIG. 5 shows optical injection of Propidium iodide (PI) with the laser-induced breakdown of a 500 nm nanoparticle positioned at an axial location of 10 μM above the cell monolayer, and cell viability assay using Calcein-AM (CAM). FIG. 5 (a) shows a brightfield image of cells immediately after the experiment. FIGS. 5 (b) and (c) show fluorescence images of PI and CAM, respectively. Cells showing both the PI and CAM signal indicate the injection of PI with retention of cell viability.

Figure 6:
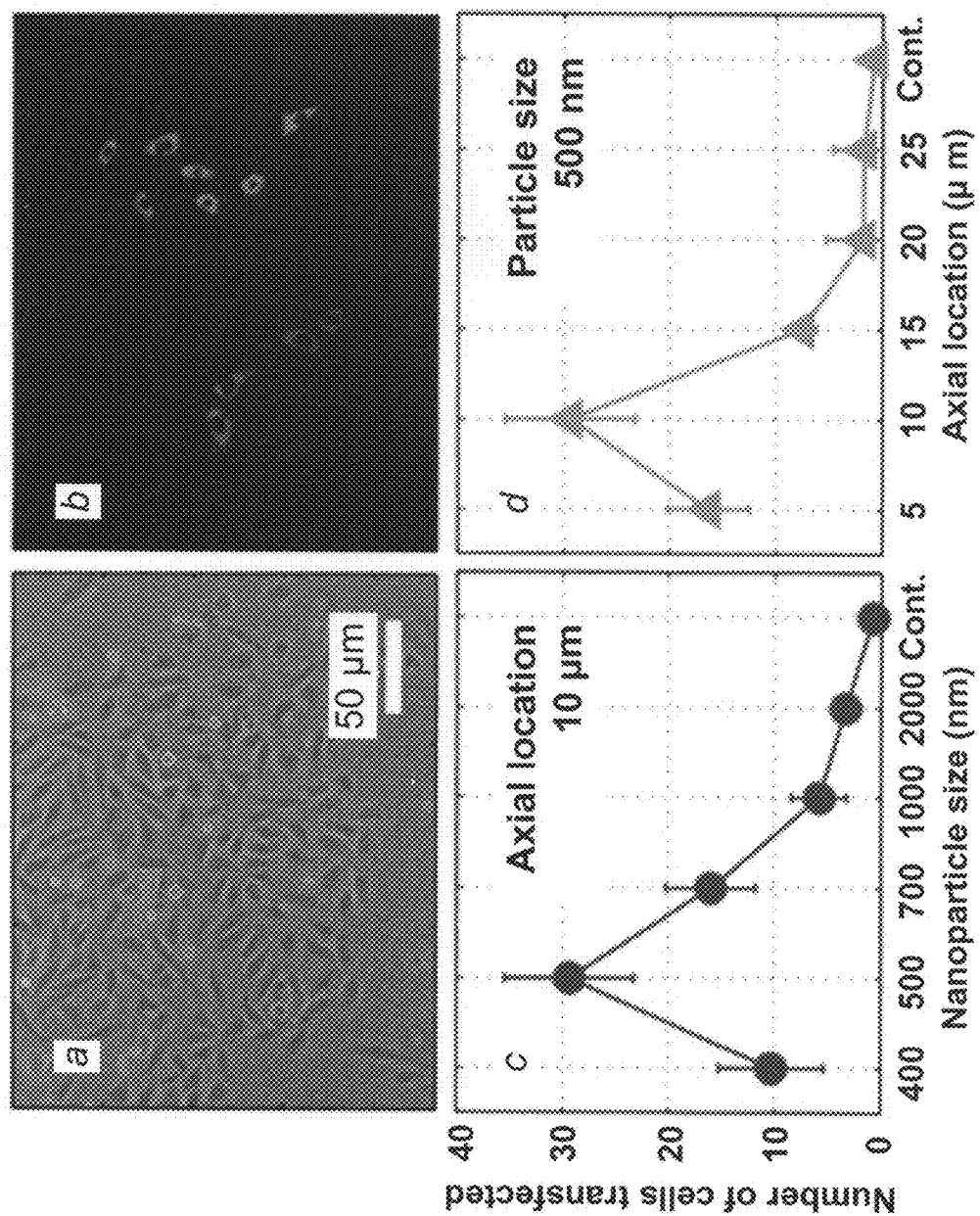
FIG. 6 shows the optimization of the transfection of Mito-DsRed encoding plasmids into CHO-K1 cells with two different parameters, namely nanoparticle size ranging from 400 nm to 2 μm, and axial location between 5 and 25 μm from the substrate.

The optimization of this technique for gene transfection was studied using two different parameters, namely nanoparticle size ranging from 400 nm to 2 μm, and axial location between 5 and 25 μm from the cell monolayer. The results of this study are shown in FIG. 6 for the transfection of Mito-DsRed encoding plasmids into CHO-K1 cells.

FIG. 6(a) shows a brightfield image of a cell monolayer, 48 hours after the experiment with the laser-induced breakdown of a 500 nm nanoparticle at an axial location of 10 μm. The corresponding fluorescence image (FIG. 6(b)) indicates a typical colony of transfected cells with the plasmid expressing the Mito-DsRed protein observed under a fluorescence microscope. The number of transfected cells was typically ~3 by the laser-induced breakdown of a single nanoparticle with the optimized parameters, which are 500 nm in nanoparticle size and 10 μm in axial location (FIG. 6(c),(d)). The control cells were exposed to the CW 1070 nm and nanosecond 532 nm lasers without any laser induced breakdown. This clearly shows these two parameters can optimize the transfection efficiency.

Figure 7:
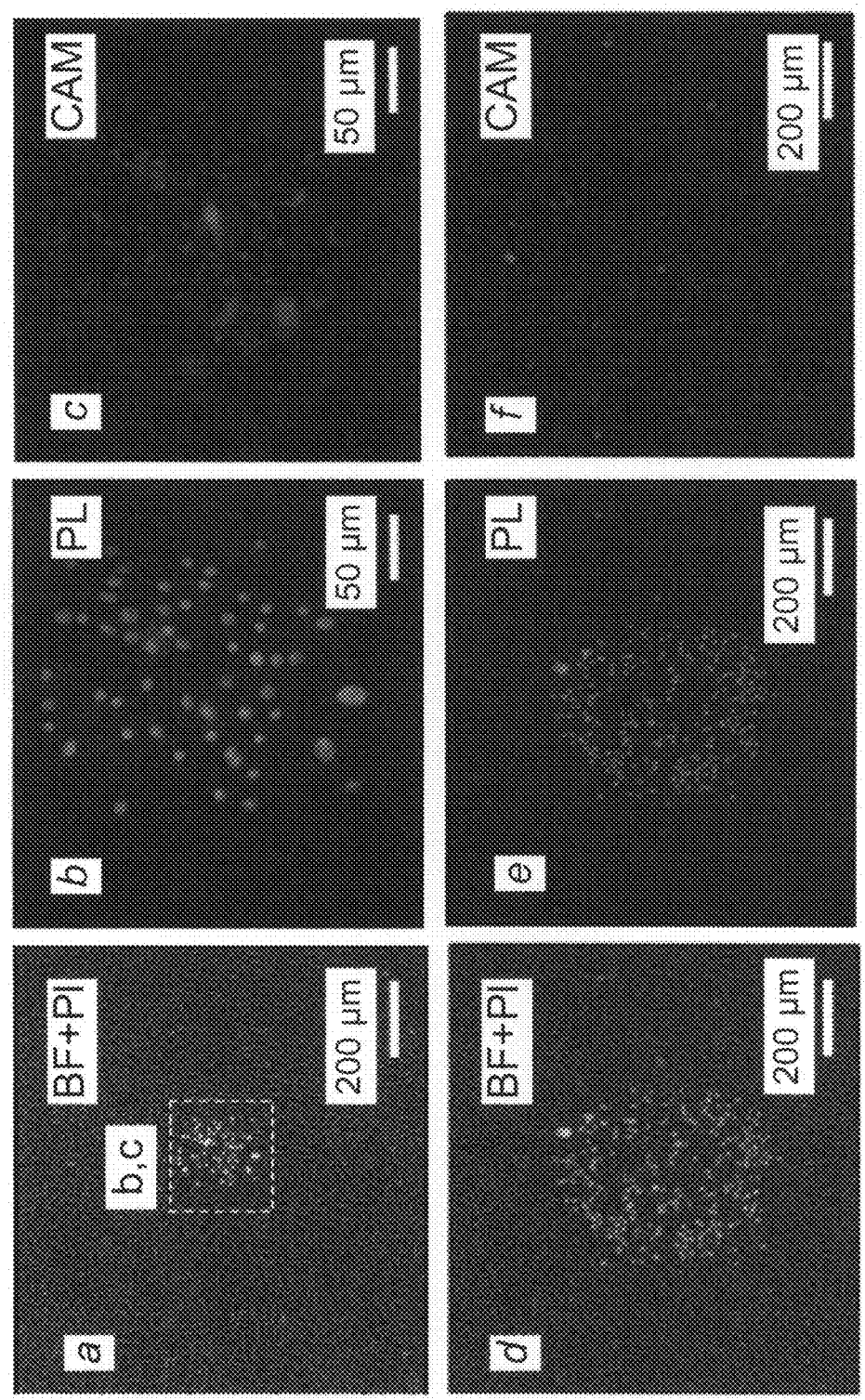
FIG. 7 shows molecular injection of PI into CHO-K1 cells in a wide area (>250 μM in diameter) by the laser-induced breakdown of a 500 nm nanoparticle.

The contribution of the acoustic transients excited by the spherical bubble collapse has not been considered. Preliminary studies have provided evidence of the role of acoustic transients to the observed cellular effects. FIG. 7 shows molecular injection of PI into multiples of CHO-K1 cells in a wide area (>250 μm in diameter) by the laser induced breakdown of a 500 nm nanoparticle. FIGS. 7 (a), (b), (d) and (e) show a large number of CHO-K1 cells (>100) injected with PI. Acoustic transients emitted from the collapsing bubble are considered to be responsible for such large scale poration. Fluorescence images of CAM indicate the cells injected with PI remain viable (FIG. 7c).

Figure 8:
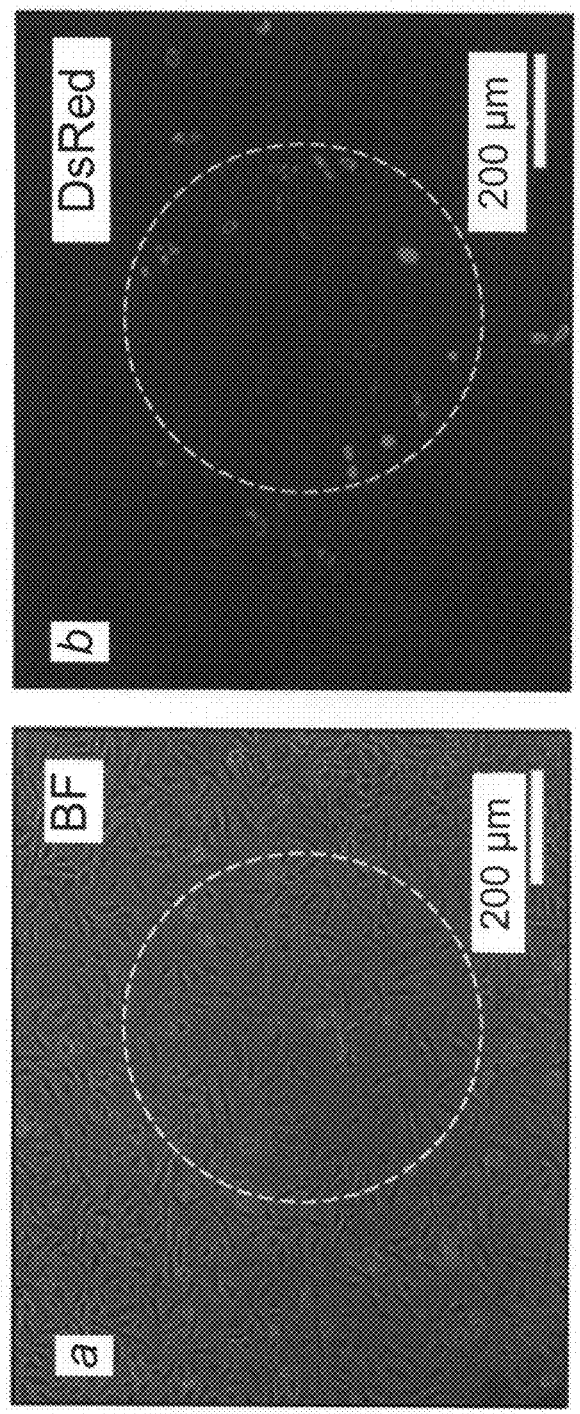
FIG. 8 shows the transfection of Mito-DsRed encoding plasmids into CHO-K1 cells in a wide area.

FIG. 8 shows the transfection of Mito-DsRed encoding plasmids into CHO-K1 cells in a wide area. FIG. 8 (a) shows a brightfield image of cells, 48 hours after the laser-induced breakdown of a 500 nm nanoparticle. FIG. 8 (b) shows the corresponding fluorescence image of transfected cells ~50.

Simultaneous multi-site targeted nanosurgery for cells or tissues by the laser-induced breakdown of single nanoparticles optically trapped at multisite using a dynamic diffractive optical element was successfully demonstrated using spatial light modulators (SLMs) (Hamamatsu, LCOS-SLM X10468).

Figure 9:
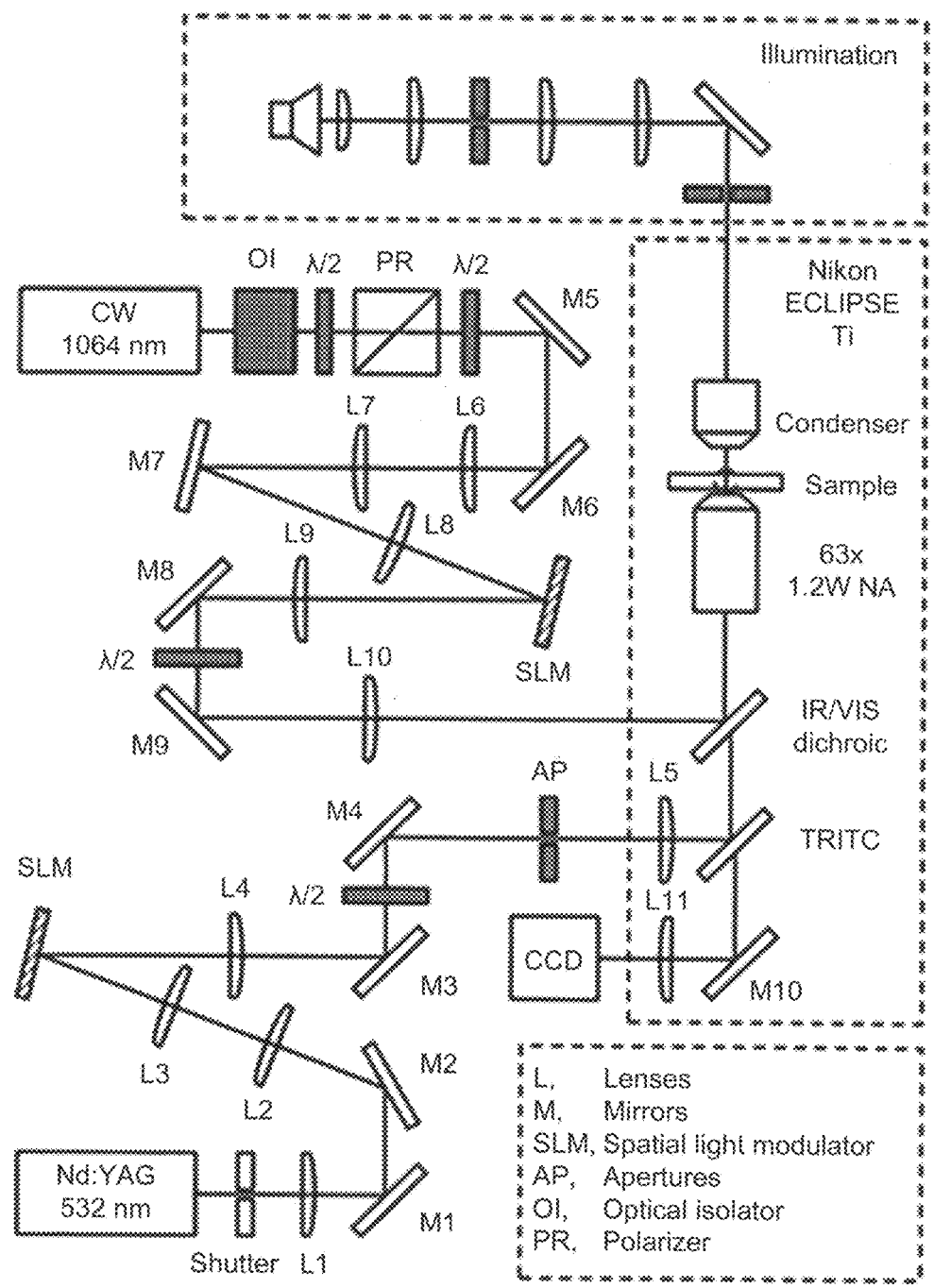
FIG. 9 is a schematic diagram of an optical arrangement for trapping and causing simultaneous laser-induced breakdown of multiple nanoparticles.

FIG. 9 shows an example of a suitable optical arrangement for simultaneous multi-site poration. This has two SLMs one each for dividing the outputs from the trapping laser and the breakdown laser into multiple beams, each beam being positioned and arranged to target one of a plurality of different sites. The same effect may also be achieved with other optical devices, such as an acousto-optic deflector. The CW 1064 (for trapping) and nanosecond 532 nm (for laser-induced breakdown) lasers were both multiplexed by the SLMs to three spots each forming an equilateral triangle with side of ~10 µm, projected onto the same focal plane of a water immersion objective (Carl Zeiss Ltd., 63×, 1.2 NA/W). The three trapped nanoparticles, each 500 nm in diameter were then targeted for breakdown by the multiplexed nanosecond laser. The results are shown in FIG. 10.

Figure 10:
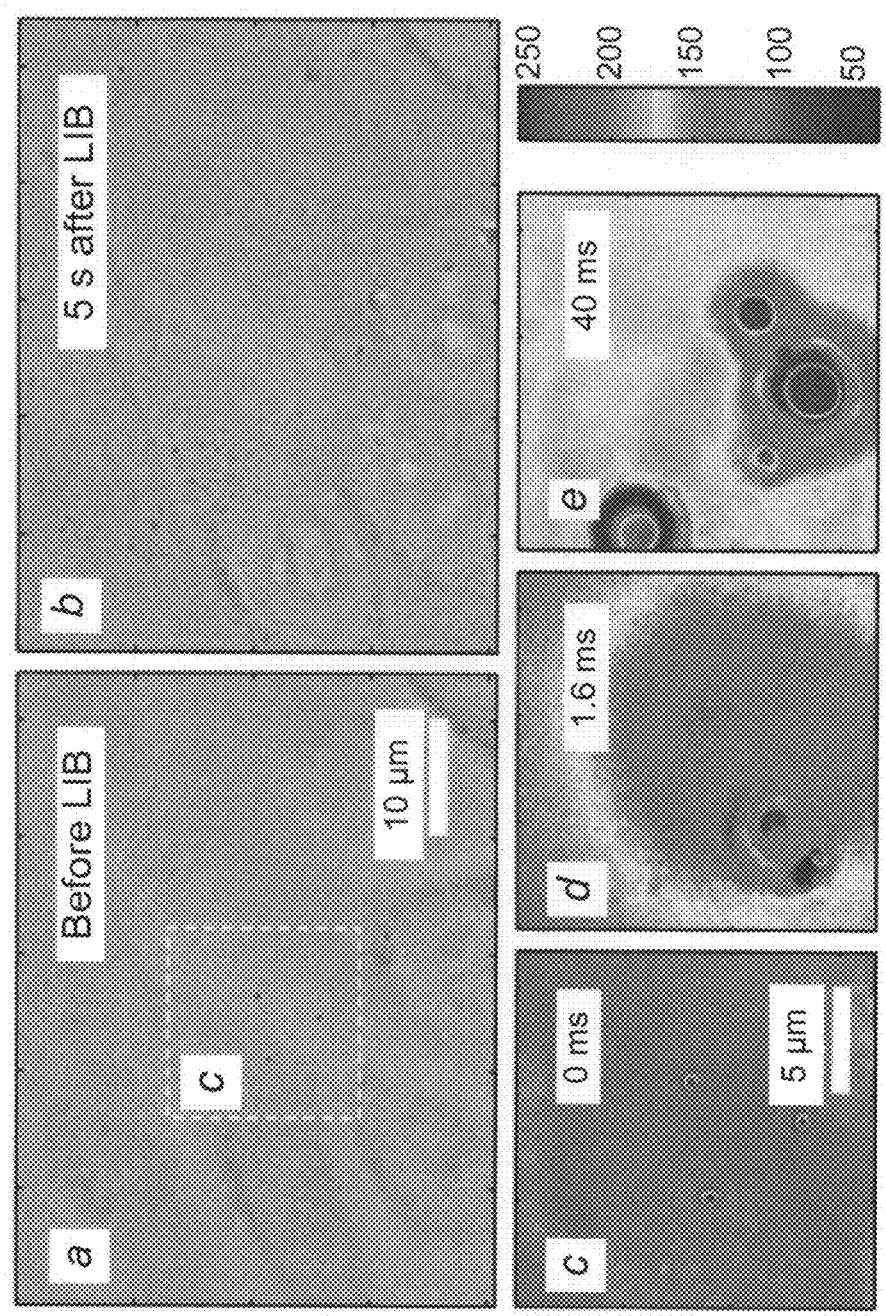
FIG. 10 shows the results of simultaneous multi-site targeted nanosurgery for CHO-K1 cells by the laser-induced breakdown of three 500 nm nanoparticles optically trapped at multiple sites using a dynamic diffractive optical element.

FIGS. 10 (a) and 10 (c) show three trapped 500 nm nanoparticles placed on an equilateral triangle with side of ~10 µm above the cell monolayer before laser-induced breakdown. FIG. 10 (b) shows cell morphology, 5 s after the experiment. FIGS. 10 (d) and (e) show time-resolved images of the laser-induced breakdown of these three trapped nanoparticles. This result suggests that the technique has the potential to allow a fully optically controlled cavitation system for multi-site targeted nanosurgery for cells or tissues in future.

The present invention uses laser-induced breakdown of optically trapped single nanoparticles to gain control over microbubble cavitation for successful molecular injection or transfection. The laser-induced cavitation bubbles, which cause the formation of a hydrodynamic jet and/or acoustic transients upon collapse, played an important role in membrane poration of cells. The kinetic jet can cause localized membrane poration of cells in a targeted area, while the acoustic transients can yield large scale poration of these cells in a wide area as the acoustic waves can propagate a long distance in the sample medium. Physical impact to cells from those microbubbles inducing membrane permeabilization of cells with retention of cell viability can be optimized by the laser-induced breakdown parameters, such as nanoparticle material and its size. With jets, multiple cell transfection can be achieved in specific targeted regions. The number of transfected cells was typically ~3 by the laser-induced breakdown of a single 500 nm nanoparticle positioned at an axial location of 10 µm above the cell monolayer. With acoustic transients, ~50 cells in a wide area >250 µm in diameter were successfully transfected by the laser-induced breakdown of a single 500 nm nanoparticle.

The invention provides a platform for the multi-site-specific transfection of multiple cells or tissues by the use of laser-induced breakdown combined with the aid of the optical trapping and SLM techniques. Unlike photoporation techniques using femtosecond laser pulses, the precise positioning of the laser focus on the cell membrane is unnecessary, yet it allows targeted transfection of multiple cells in a specific area. The laser-induced breakdown condition suitable for high-throughput transfection can be optimized by the laser-induced breakdown parameters.

The present invention has the potential to increase cell transfection capability, avoiding cell lysis, with consequent advantages in its simplicity, lower cost and higher reliability than existing methods. It can also achieve the targeted transfection of multiple cells in a specific zone by the hydrodynamic jets, or allows large scale transfection of cells in a wide area by the acoustic transients depending on the laser-induced breakdown condition. Consolidation of the optical trapping and laser-induced breakdown allows a fully optically controlled microbubble cavitation system for simultaneous and multi-site targeted nanosurgery for cells or tissues when coupled with a dynamic diffractive optical element.

A skilled person will appreciate that variations of the disclosed arrangements are possible without departing from the invention. For example, whilst the invention is described with reference to cell poration, it could be used for the poration of other biological material or tissue. Indeed, it could be used for the poration of non-biological material, for example, any material that has an outer membrane. Accordingly the above description of the specific embodiment is made by way of example only and not for the purposes of limitation. It will be clear to the skilled person that minor modifications may be made without significant changes to the operation described.

The invention claimed is:

1. A system for porating one or more cells, the system comprising:
   at least one laser for creating an optical trap for optically trapping a particle so as to position the particle near at least one cell; and
   at least one laser for producing a laser beam to be directed onto the optically trapped particle for causing laser-induced breakdown of the optically trapped particle to create one or more cavitations, wherein the one or more cavitations cause poration of the at least one cell.

2. A system as claimed in claim 1 wherein the at least one laser for causing laser-induced breakdown comprises a pulsed laser.

3. A system as claimed in claim 1 wherein the particle is made of a material selected from: silica; polystyrene; latex; gold; silver; or carbon.

4. A system as claimed in claim 1 wherein the particle is shaped as a sphere or shell or rod.

5. A system as claimed in claim 1 that is adapted to porate multiple cells using the laser-induced breakdown of a single particle.

6. A system as claimed in claim 1 wherein multiple nanoparticles are provided and the at least one laser for causing laser-induced breakdown are operable to simultaneously cause breakdown of the multiple nanoparticles.

7. A system as claimed in claim 6 comprising an optical element for generating multiple beams from a single one of the at least one lasers for trapping the multiple nanoparticles.

8. A system as claimed in claim 6 comprising an optical element for generating multiple beams from a single one of the at least one lasers for causing laser induced breakdown of the multiple nanoparticles.

9. A system as claimed in claim 6 comprising an optical element to generate multiple beams from a single one of the at least one lasers for causing laser induced breakdown of the multiple nanoparticles and to generate multiple beams from another one of the at least one lasers for causing laser induced breakdown of the multiple nanoparticles.

10. A system as claimed in claim 7 wherein the optical element is a diffractive optical element, for example a spatial light modulator, or an acousto optic deflector.

11. A system as claimed in claim 1 wherein the optically trapping of the particle positions the particle close to a hard surface before the occurrence of the induced breakdown.

12. A system as claimed in claim 1 wherein the particle has a dimension of less than or equal to 1 micrometer to match the diffraction limited focal spot size of the breakdown laser.

13. A system as claimed in claim 1 wherein the at least one laser for causing laser-induced breakdown comprises a pulsed laser for generating optical pulses having a pulse energy of approximately 1 µJ.

14. A system as claimed in claim 13 wherein the at least one laser for causing laser-induced breakdown comprises a pulsed laser for generating optical pulses having a pulse duration of approximately 1 ns.

15. A method for porating one or more cells using the system of claim 1, the method comprising:
using the at least one laser for optically trapping a particle to optically trap a particle at a position near at least one cell; and
directing a laser beam from the at least one laser for causing laser-induced breakdown onto the optically trapped particle, thereby causing laser-induced breakdown of the optically trapped particle to create one or more cavitations, wherein the one or more cavitations cause poration of the at least one cell.

16. A method as claimed in claim 15 wherein the particle has one or more dimensions in a nanometer range.

17. A method as claimed in claim 15 comprising applying pulses of laser light to the trapped particle to cause laser-induced breakdown.

18. A method as claimed in claim 15 wherein the particle is made of a material selected from: silica; polystyrene; latex; gold; silver; or carbon.

19. A method as claimed in claim 15 wherein the particle is shaped as a sphere or shell or rod.

20. A method as claimed in claim 15 comprising porating multiple cells using the laser-induced breakdown of a single particle.

21. A method as claimed in claim 15 wherein multiple nanoparticles are provided and wherein the method involves simultaneously causing laser-induced breakdown of the multiple nanoparticles.

22. A method as claimed in claim 21 wherein the at least one laser for trapping the multiple nanoparticles comprises a single laser for trapping the multiple nanoparticles and the method comprises using an optical element to generate multiple beams from the single laser for trapping the multiple nanoparticles.

23. A method as claimed in claim 21 wherein the at least one laser for causing laser induced breakdown of the multiple nanoparticles comprises a single laser for causing laser induced breakdown of the multiple nanoparticles and the method comprises using an optical element to generate multiple beams from the single laser for causing laser induced breakdown, to thereby cause breakdown of the multiple nanoparticles.

24. A method as claimed in claim 21 wherein the at least one laser for causing laser induced breakdown of the multiple nanoparticles comprises two separate lasers for causing laser induced breakdown of the multiple nanoparticles and the method comprises using an optical element to generate multiple beams from one of the two separate lasers for causing laser induced breakdown of the multiple nanoparticles and using the same optical element to generate multiple beams from another one of the two separate lasers for causing laser induced breakdown of the multiple nanoparticles.

25. A method as claimed in claim 22 wherein the optical element is a diffractive optical element, for example a spatial light modulator, or an acousto optic deflector.

26. A method as claimed in claim 15 comprising positioning the particle close to a hard surface before causing laser induced breakdown.

27. A method as claimed in claim 15 wherein the particle has a dimension of 1 micrometer; preferably less than or equal to 500 nm to match the diffraction limited focal spot size of the breakdown laser.

* * * * *